(12) United States Patent
Wang et al.

(10) Patent No.: US 8,512,996 B2
(45) Date of Patent: Aug. 20, 2013

(54) **CELL FOR PREPARING COMPETENT CELL, METHOD FOR PREPARING COMPETENT CELL AND BACTERIAL STRAIN OF *ESCHERICHIA COLI***

(75) Inventors: Jia-Hung Wang, Taichung County (TW); Meng-Yin Tsai, Taipei (TW); Ting-Ting Hung, Yilan County (TW); Kelly Teng, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 199 days.

(21) Appl. No.: 12/979,079

(22) Filed: Dec. 27, 2010

(65) Prior Publication Data

US 2012/0149090 A1 Jun. 14, 2012

(30) Foreign Application Priority Data

Dec. 14, 2010 (TW) ................. 99143653 A

(51) Int. Cl.
  *C12N 1/20* (2006.01)
  *C12N 15/00* (2006.01)
  *C12N 15/74* (2006.01)
  *C12N 9/00* (2006.01)
  *C12Q 1/68* (2006.01)
  *C07H 21/04* (2006.01)

(52) U.S. Cl.
  USPC ............... 435/252.33; 435/252.8; 435/320.1; 435/6.1; 435/440; 435/183; 435/471; 536/23.2

(58) Field of Classification Search
  None
  See application file for complete search history.

(56) References Cited

U.S. PATENT DOCUMENTS

| 4,981,797 | A  | 1/1991  | Jessee et al. |
| 6,960,464 | B2 | 11/2005 | Jessee et al. |
| 7,648,832 | B2 | 1/2010  | Jessee et al. |

FOREIGN PATENT DOCUMENTS

| CN | 101264062   | 9/2008 |
| TW | 201014915 A | 4/2010 |

OTHER PUBLICATIONS

Purvis et al. Enhanced trehalose production improves growth of *Escherichia coli* under osmotic stress. Appl Environ Microbiol. Jul. 2005;71(7):3761-9.*
Horlacher et al. Characterization of a cytoplasmic trehalase of *Escherichia coli*. J Bacteriol. Nov. 1996;178(21):6250-7.*
Giaever et al. Biochemical and genetic characterization of osmoregulatory trehalose synthesis in *Escherichia coli*. J Bacteriol. Jun. 1988;170(6):2841-9.*
Mandel et al., "Calcium-dependent Bacteriophage DNA Infection," J. Mol. Biol., 1970, pp. 159-162, vol. 53.
Hanahan, "Studies on Transformation of *Escherichia coli* with Plasmids," J. Mol. Biol., 1983, pp. 557-580, vol. 166.
Inoue, "High efficiency transformation of *Escherichia coli* with plasmids," Gene, 1990, pp. 23-28, vol. 96.
Seo et al., "Chracterization of a Bifunctional Enzyme Fusion of Trehalose-6-Phosphate Synthetase and Trehalose-6-Phospahte Phosphatase of *Escherichia coli*," Applied and Environmental Microbiology, Jun. 2000, pp. 2484-2490, vol. 66, No. 6.
Dufee et al., "The Complete Genome Sequence of *Escherichia coli* DH10B: Insights into the Biology of a Laboratory Workhorse," Journal of Bacteriology, Apr. 2008, pp. 2597-2606, vol. 190, No. 7.
P. Rattanachaikunsopon et al., "Glass bead-based transformation method for lactic acid bacteria," Science-Asia 35 (2009) 234-241.
W. Boos et al., "Trehalose Transport and Metabolism in *Escherichia coli*," Journal of Bacteriology, Jun. 1990, 2450-3461.
D. Hanahan et al., "Plasmid Transformation of *Escherichia coli* and Other Bacteria," Methods in Enzymology, vol. 204, 63-64, 1991.
Sambrook et al., Molecular Cloning: A Laboratory Manual, Chapter 1: Plasmids and Their Usefulness in Molecular Cloning, Protocol 22 Ligating Plasmid and Target DNAs in Low-melting-temperature Agarose, 2001, pp. 1.103-1.104.

* cited by examiner

*Primary Examiner* — Yong Pak
(74) *Attorney, Agent, or Firm* — Muncy, Geissler, Olds & Lowe, PLLC

(57) ABSTRACT

The invention provides a cell for preparing competent cells, wherein the cell is capable of spontaneously accumulating self-producing trehalose therein and the cell is used for the preparation of competent cells. The invention also provides a method for preparing competent cells, including: culturing the cell for preparing the competent cell mentioned previously to obtain a cell suspension; placing the cell suspension into an ice bath; centrifuging the cell suspension to obtain a cell precipitate; mixing a transform reagent with the cell precipitate; and obtaining competent cells suspension.

7 Claims, 4 Drawing Sheets

CELL FOR PREPARING COMPETENT CELL, METHOD FOR PREPARING COMPETENT CELL AND BACTERIAL STRAIN OF *ESCHERICHIA COLI*

CROSS REFERENCE TO RELATED APPLICATIONS

This Application claims priority of Taiwan Patent Application No. 099143653, filed on Dec. 14, 2010, the entirety of which is incorporated by reference herein.

INCORPORATION BY REFERENCE OF SEQUENCE LISTING

A sequence listing submitted as a text file via EFS-Web is incorporated herein by reference. The text file containing the sequence listing is named "0954-A23635-US_Seq_Listing.txt"; its date of creation was Dec. 24, 2010; and its size is 16K bytes.

BACKGROUND OF THE INVENTION

1. Field of the Invention

The present invention relates to a cell for preparing competent cells, and in particular relates to a cell which is capable of spontaneously accumulating self-producing trehalose therein and a method for preparing competent cells by using the cell.

2. Description of the Related Art

The process of introducing a DNA molecule carrying a genetic message into a host cell is called "transformation". Moreover, a host cell which is pre-treated with a physical or chemical treatment and consequently has a property of enabling a DNA molecule to enter therein, easily, is called "competent cells". In the molecular biology field and genetic engineering operation, in order to enable a host cell to perform a duplication or expression of a specific DNA or protein, obtainment of competent cells which is able to be easily transformed with DNA, is an important and essential process.

Since *Escherichia coli* cells have advantages of being able to rapidly grow, be cultured easily and be investigated thoroughly, at present, it is a microorganism which is most popularly used as a host cell in many biotechnology related experiments. For recent progress of genetic engineering technology, there have been many methods for preparing *Escherichia coli* competent cells for the transformation process and transformation, such as the $CaCl_2$ chemical transformation process published by Mandel, M and Higa A. (J. Mol. Biol. 166:557) in 1970 and the transformation process improvements by adding other kinds of cations with different concentrations and an anti-freezing agent into a transformation agent, successively published by Hanahan, D. (J. Mol. Biol. 166:557) in 1983 and by Inoue, H. (Gene 96:23) in 1990. Presently, high transformation process transformation efficiency is $10^8$ transformants/µg plasmid DNA.

However, competent cells which can be transformed, generated from the methods for preparing *Escherichia coli* competent cells mentioned above, must be stored under a temperature of about −70° C. to −80° C. to prevent an obvious decrease in the transformation efficiency of the competent cells after the competent cells are stored for several months.

In recent years, a technique for preparing relatively stable competent cells at temperature has been developed by Life Technologies Corporation (USA), wherein the competent cells do not have to be stored at a temperature of about −70° C. to −80° C., to hold transformation efficiency of the competent cells stable. The process of the technique comprises adding a specific carbohydrate or chemical polymer to an agent for preparing and storing competent cells as an anti-freezing agent, and thus the competent cells are able to be stored at a higher temperature (such as −20° C.) without obviously reducing the transformation efficiency of the competent cells. Although, compared with the conventional method, the technique saves more energy and the competent cells are transported more easily, the addition of the additional specific anti-freezing agent raises the cost for preparing the competent cells.

Accordingly, a new component and method for preparing competent cells is needed, wherein the competent cell is able to be stored at a higher temperature, to have advantages of saving energy, being of low cost and being able to be transported easily. The new component and method for preparing competent cells, should make the gene transformation technique for organism cells easier.

BRIEF SUMMARY OF THE INVENTION

The invention provides a cell for preparing competent cells, wherein the cell is capable of spontaneously accumulating self-producing trehalose therein and the cell is used for the preparation of competent cells.

The invention also provides a bacterial strain of *Escherichia coli* deposited in the German Collection of Microorganisms and Cell Cultures (DSMZ) under Accession number DSM 24175, wherein the bacterial strain of *Escherichia coli* is capable of spontaneously accumulating self-producing trehalose therein.

The invention further provides a method for preparing competent cells, comprising: culturing the cell for preparing the competent cell to obtain a cell suspension; placing the cell suspension into an ice bath; centrifuging the cell suspension to obtain a cell precipitate; mixing a pre-treating agent with the cell precipitate; and obtaining competent cells suspension.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
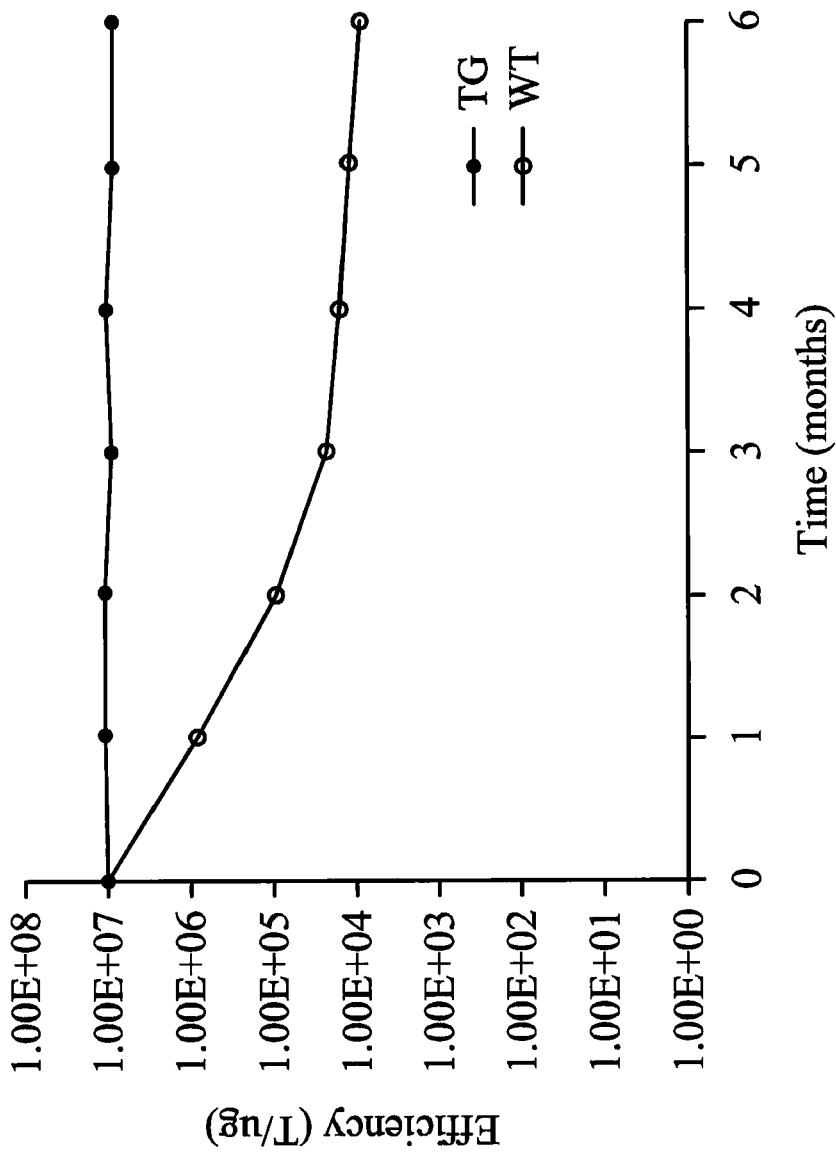
FIG. 1 is a diagram of curves showing stability differences between the transformation efficiency of a WT competent cell suspension and a TG competent cell suspension during a 6 month storage period under a temperature of −20° C.

The following description is of the best-contemplated mode of carrying out the invention. This description is made for the purpose of illustrating the general principles of the invention and should not be taken in a limiting sense. The scope of the invention is best determined by reference to the appended claims.

In one aspect of the invention, the invention provides a cell capable of spontaneously accumulating self-producing trehalose therein, and the cell is used for the preparation of competent cells. Accumulation of trehalose in a cell, prevents intracellular protein accumulation and denaturalization, due to low temperatures, to occur therein, and has a stabilizing effect on a cell membrane of the cell. Therefore, as compared with prior art, competent cells prepared from the cell of the invention is able to be stored in a relatively high temperature environment with high transformation efficiency, wherein no additional specific carbohydrates or chemical polymers are added as an anti-freezing agent.

The phrase "self-producing trehalose" used herein means trehalose produced within a cell, not trehalose additionally added into a culture medium for culturing a cell.

The cell of the invention may be obtained by performing a mutagenesis-selection process or a genetic engineering modification of a microorganism, but is not limited thereto. The microorganism may comprise *Escherichia coli*, yeast or mold. The *Escherichia coli* may comprise DH5α, JM109, XL1-Blue, HB101 or BL21, etc.

In one embodiment, the cell of the invention may be obtained by performing genetic engineering modification of a microorganism. The genetic engineering genetic engineering modification may comprise enabling the microorganism to over-express at least one endogenous gene encoding a trehalose-synthesis related enzyme and/or knocking-out at least one endogenous gene encoding a trehalose-decomposition related enzyme from the microorganism, and/or transferring at least one exogenous gene encoding a trehalose-synthesis related enzyme into a genome of the microorganism. In one embodiment, enabling the microorganism (as a target microorganism) to over-express at least one endogenous gene encoding a trehalose-synthesis related enzyme is accomplished by introducing a nucleotide sequence into a target microorganism, wherein the nucleotide sequence is identical or similar to a specific gene nucleotide sequence in the genome of the microorganism.

The genetic engineering modification of a microorganism may be performed by a conventional recombination technique (see, such as Sambrook et al., Molecular Cloning: A Laboratory Manual, Cold Spring Harbor Laboratory Press.).

In one embodiment, the genetic engineering modification of a microorganism may be performed by the following method. By performing a polymerase chain reaction, the nucleotide sequence of the at least one gene encoding a trehalose-synthesis related enzyme is obtained from a microorganism belonging to a species identical to that thereof, and/or by performing a polymerase chain reaction, wherein the nucleotide sequence of the at least one gene encoding a trehalose-synthesis related enzyme is obtained from a microorganism belonging to a species different from that thereof. The information of the enzyme gene desired, may be found in a database, such as the GenBank. If it is needed, according to the differences between the target microorganism respectively used, a sequence encoding optimization process may be performed to the obtained sequence to gain a subsequent best use of the sequence in the target microorganism (as a host microorganism).

After that, the nucleotide sequence of the at least one gene encoding a trehalose-synthesis related enzyme from the microorganism belonging to the species identical to that thereof and/or the nucleotide sequence of the at least one gene encoding a trehalose-synthesis related enzyme from the microorganism belonging to the species different from that thereof are/is inserted into an appropriate expression vector to generate a DNA construct expressing the enzyme mentioned previously.

Alternatively, two ends of a gene expression cassette formed in the foregoing DNA construct are further ligated with a nucleotide sequence, respectively, wherein the nucleotide sequence is able to recombine/cross over with a nucleotide sequence of a gene encoding a trehalose-decomposition related enzyme to further delete the nucleotide sequence of the gene encoding the trehalose-decomposition related enzyme.

Alternatively, a nucleotide sequence is prepared, wherein the nucleotide sequence is able to recombine/cross over with a nucleotide sequence of a gene encoding a trehalose-decomposition related enzyme, in a genome of a target microorganism, to further delete the nucleotide sequence of the gene encoding the trehalose-decomposition related enzyme.

Then, the foregoing gene expression cassette contained in the DNA construct or the foregoing nucleotide is able to recombine/cross over with a nucleotide sequence of a gene encoding a trehalose-decomposition related enzyme, in a genome of a target microorganism, to further delete the nucleotide sequence of the gene encoding the trehalose-decomposition related enzyme, is introduced into a target microorganism, and a positive transformant is selected to obtain a genetic engineering modified cell of the invention.

Furthermore, by using methods known in the field, such as immunoblot blot method and enzyme activity analysis, the over-expression or silent deletion mentioned above of the gene or gene transformation may be confirmed.

The phrase "a trehalose-synthesis related enzyme" used herein refers to an enzyme which participates in the synthesis of trehalose (for example, trehalose-synthesis related enzyme of *Escherichia coli* described in Seo et al., Appl. Environ. Microbiol., 66 (6):2484-2490, 2000), and the enzyme is a single enzyme or an enzyme group and functional equivalents thereof which is/are capable of converting other molecules into a trehalose by at least one reaction step.

In one embodiment, the trehalose-synthesis related enzyme may comprise, but is not limited to, trehalose-6-phosphate synthase (TPS) (EC 2.4.1.15), trehalose-6-phosphate phosphatase (TPP) (EC 3.1.3.12), α,α-trehalose-phosphate synthase (UDP-forming) (EC 2.4.1.15), α,α-trehalose synthase (EC 2.4.1.245), trehalose-phosphatase (EC 3.1.3.12), 4-alpha-D-((1→4)-alpha-D-glucano)trehalose trehalohydrolase (EC 3.2.1.141), (1→4)-α-D-glucan 1-α-D-glucosylmutase (EC 5.4.99.15), α-D-glucosyltransferase (EC 5.4.99.16) and/or functional equivalents thereof, etc. The detailed information about the trehalose-synthesis related enzyme is shown in Table 1.

TABLE 1

Exemplificative trehalose-synthesis related enzyme

| Enzyme | Enzyme Commission number (EC Number) | Organism source |
| --- | --- | --- |
| trehalose-6-phosphate synthase (TPS) | EC 2.4.1.15 | *Escherichia coli* |
| trehalose-6-phosphate phosphatase (TPP) | EC 3.1.3.12 | *Escherichia coli* |
| α,α-trehalose-phosphate synthase (UDP-forming) | EC 2.4.1.15 | *Drosophila, Arabidopsis, Populus, Ricinus, Saccharomyces, Escherichia coli, Salmonella* |

TABLE 1-continued

Exemplificative trehalose-synthesis related enzyme

| Enzyme | Enzyme Commission number (EC Number) | Organism source |
|---|---|---|
| α,α-trehalose synthase | EC 2.4.1.245 | *Nitrosococcus halophilus, Acidithiobacillus* |
| trehalose-phosphatase | EC 3.1.3.12 | *Drosophila, Arabidopsis, Saccharomyces, Escherichia coli* |
| 4-alpha-D-((1→4)-alpha-D-glucano)trehalose trehalohydrolase | EC 3.2.1.141 | *Pseudomonas, Nitrosococcus, Acidithiobacillus, Agrobacterium, Deinococcus* |
| (1→4)-α-D-glucan 1-α-D-glucosylmutase | EC 5.4.99.15 | *Pseudomonas, Nitrosococcus, Acidithiobacillus, Agrobacterium, Deinococcus* |
| α-D-glucosyltransferase | EC 5.4.99.16 | *Deinococcus, Pseudomonas, Mycobacterium, Streptomyces* |

The phrase "a trehalose-decomposition related enzyme" used herein refers to an enzyme which participates in the decomposition of trehalose (for example, that described in Durfee et al., J. Bacteriol., 190 (7):2597-2606, 2008), and the enzyme is a single enzyme or an enzyme group and functional equivalents thereof which is/are capable of converting a trehalose into other small molecule sugars.

In one embodiment, the trehalose-decomposition related enzyme may comprise, but is not limited to, cytoplasmic trehalase, periplasmic trehalase, and/or functional equivalents thereof, etc.

The phrases "an endogenous enzyme gene", "an endogenous gene encoding an enzyme" and similar phrases thereof used herein refer to a specific enzyme gene in a genome of a target microorganism, or refer to a gene encoding an enzyme, wherein the nucleotide sequence of the gene is identical or similar to a nucleotide sequence of a specific enzyme gene in a genome of a target microorganism. The phrases "an exogenous enzyme gene", "an exogenous gene encoding an enzyme" and similar phrases thereof used herein refer to a specific enzyme gene from a genome of a microorganism belonging to a species different from that of a target microorganism.

In one embodiment, the cell of the invention may be obtained by enabling an *Escherichia coli* DH5α cell to over-express at least one endogenous gene encoding a trehalose-synthesis related enzyme and knocking-out at least one endogenous gene encoding a trehalose-decomposition related enzyme from the *Escherichia coli* DH5α cell. In the embodiment, the trehalose-synthesis related enzyme may comprise trehalose-6-phosphate synthase and trehalose-6-phosphate phosphatase. The amino sequence of the trehalose-6-phosphate synthase and the amino sequence of the trehalose-6-phosphate phosphatase may be SEQ ID. No.: 1 and SEQ ID. No.: 2, respectively. A nucleotide sequence encoding the rehalose-6-phosphate synthase may be SEQ ID. No.: 3 or a sequence having at least 80% sequence homology to the SEQ ID. No.: 3, and a nucleotide sequence encoding the trehalose-6-phosphate phosphatase may be SEQ ID. No.: 4 or a sequence having at least 80% sequence homology to the SEQ ID. No.: 4. Furthermore, the trehalose-decomposition related enzyme may comprise cytoplasmic trehalase or periplasmic trehalase. A nucleotide sequence encoding the cytoplasmic trehalase may be SEQ ID. No.: 5 (tre F) or a sequence having 80% sequence homology to the SEQ ID. No.: 5, and a nucleotide sequence encoding the periplasmic trehalase may be SEQ ID. No.: 6 (tre A) or a sequence having 80% sequence homology to the SEQ ID. No.: 6. A sequence having at least 80% sequence homology to a SEQ ID. No. refers to a sequence after a plurality of bases are added thereto, deleted therefrom and/or replaced therewith, while still having at least 80% of nucleotides identity to the SEQ ID. No. The sequence homology of at least two sequences may be obtained by comparing the at least two sequences with each other by a well known software, such as the BLAST (http://blast.ncbi.nlm.nih.gov/Blast.cgi) and the FASTA (http://www.ebi.ac.uk/Tools/sss/fasta/) software, etc.

In another embodiment, the cell of the invention may be obtained by introducing a nucleotide sequence encoding the rehalose-6-phosphate synthase and a nucleotide sequence encoding the trehalose-6-phosphate phosphatase into an *Escherichia coli* DH5α cell, and knocking-out a gene encoding the cytoplasmic trehalase from a gemone of the *Escherichia coli* DH5α cell, wherein the nucleotide sequence encoding the rehalose-6-phosphate synthase and the nucleotide sequence encoding the trehalose-6-phosphate phosphatase are SEQ ID. No.: 3 and SEQ ID. No.: 4, respectively, while the nucleotide sequence encoding the cytoplasmic trehalase is SEQ ID. No.: 5. The *Escherichia coli* DH5α cell obtained by the method is named *Escherichia coli* EcDTre001, and was deposited on Nov. 11, 2010, in the German Collection of Microorganisms and Cell Cultures (Deutsche Sammlung von Mikroorganismen and Zellkulturen GmbH, DSMZ) under Accession number DSM 24175.

Competent cells prepared from the cell of the invention may be capable of being stored at a temperature of lower than −10° C., preferably under a temperature of −20° C. or lower. In addition, transformation efficiency of the competent cell prepared from the cell of the invention may reach about $10^7$-$10^9$ transformants/μg plasmid DNA.

According to the above-mentioned, the cell of the invention has potential to be competent cells with low manufacturing cost and high transformation efficiency. Therefore, in another aspect of the invention, the invention provides a use of the cell of the invention, which is capable of spontaneously accumulating self-producing trehalose therein, for preparing of competent cells. Moreover, the invention further provides a new bacterial strain of *Escherichia coli* which is named as EcDTre01, which was deposited on Nov. 11, 2010, in the German Collection of Microorganisms and Cell Cultures (DSMZ), located at Inhoffenstrasse 7B, Braunschweig, Germany, 38124, under Accession number DSM 24175, and provides a use of the bacterial strain of *Escherichia coli* for preparing of competent cells, wherein the bacterial strain of *Escherichia coli* is capable of spontaneously accumulating self-producing trehalose therein.

In further another aspect of the invention, the invention provides a method for preparing competent cells, wherein the method may comprise the following steps.

First, a cell of the invention is cultured to obtain a cell suspension. In one embodiment, a temperature for culturing the cell may be about 20-40° C., preferably about 37° C. Furthermore, in one embodiment, time for culturing the cell may be about 12-18 hours, preferably about 16 hours. In one embodiment, the cell may be the cell deposited in the German Collection of Microorganisms and Cell Cultures (DSMZ) under Accession number DSM 24175.

Next, the cell suspension obtained from the first steps is placed into an ice bath. In one embodiment, a temperature of the ice bath may be about 0-10° C., preferably about 0-4° C. In addition, time for holding the cell suspension in the ice bath may be about 0-120 minutes, preferably about 20 minutes.

Then, after performing the ice bath step to the cell suspension, the cell suspension is centrifuged to obtain a cell precipitate.

After that, a pre-treating agent is mixed with the cell precipitate. The pre-treating agent may comprise any agent which enables a host cell to more easily allow a DNA molecule to enter therein. In one embodiment, the pre-treating agent may comprise a pre-treating agent conventionally used in the calcium-chloride method, or any such as the prepared and used pre-treating agent described in Mandel, M. and Higa A. (J. Mol. Biol. 53:159)(1970) or Inoue, H. (Gene 96:23) (1990).

After the transformation agent is well mixed with the cell precipitate, competent cells suspension is obtained, wherein the competent cell suspension contains competent cells formed from the cell of the invention.

The competent cell suspension obtained from the foregoing method is capable of being stored at a temperature of lower than about −10° C., preferably about −10° C. to −130° C. In one embodiment, the competent cell suspension is capable of being stored at a temperature of about −20° C.

Furthermore, in one embodiment, the foregoing method for preparing competent cells of the invention may further comprise adding at least one solid sphere into the competent cell suspension. The solid sphere may be germ-free or sterilized. A forming material of the solid sphere may be a material with a thermal conductivity better than that of the transformation agent (liquid state), such as glass, ceramics, stainless steel, iron or aluminum, etc., but is not limited thereto. A particle diameter of the solid sphere may be about 2-6 mm, preferably about 3-5 mm.

One skilled in the art knows that when a standard transformation process is performed to the prepared competent cell, heat shock is a step, which can be used to raise the permeability of the competent cell. Heat shock is a simple and effective step, however, when the performing time thereof is too long, it will result in cell weakness, and when the performing time thereof is too short, it will result in insufficient permeability of the competent cell. Moreover, cell suspension in a tube is not easily uniformly heated, such that transformation efficiency of the competent cell may be significantly reduced.

In the invention, a solid sphere with good thermal conductivity is added into the obtained competent cell suspension so that the heat shock performing time is reduced and the cells in the tube are more uniformly heated. Therefore, a stable transformation efficiency of the competent cell is able to be obtained because the competent cell has good permeability and little heat damage. Moreover, the solid sphere added into the competent cell suspension may be directly used as a spreader for spreading the competent cell suspension on a plate, and thus as compared with the conventional method, the method of the invention has advantages of a shorter time, convenience, and substantially reducing contamination probability. In one embodiment, adding the solid sphere with good thermal conductivity into the competent cell suspension enables the transformation efficiency of the competent cell to be increased 3 to 10 times. In other words, the transformation efficiency of the competent cell may reach $10^9$ transformants/µg plasmid DNA.

EXAMPLE

Material and Methods

1. Preparation of the Cell Capable of Spontaneously Accumulating Self-Producing Trehalose Therein of the Invention A *Escherichia coli* genomic DNA was used as a template, and the following two pairs of DNA sequence segments were designed and used as two pairs of primers. A polymerase chain reaction of the *Escherichia coli* genomic DNA was conducted by using the two pairs of primers to obtain an entire nucleotide sequence of a gene of a trehalose-synthesis related enzyme, trehalose-6-phosphate synthase (SEQ ID. No.: 3), and an entire nucleotide sequence of a gene of a trehalose-synthesis related enzyme, trehalose-6-phosphate phosphatase (SEQ ID. No.: 4).

```
(P1f) TPS-RE_F:
                                     (SEQ ID. No.: 7)
      GGACTAGTCCCCCCCGGGGGATGAGTCGTTTAGTCGTAGT (P1r) TPS-L_R:
                                     (SEQ ID. No.: 8)
      TCCGCGCTGCGGCTGCCCAGCGCAAGCTTTGGAAAGGTAG (P2f) TPP-L_F:
                                     (SEQ ID. No.: 9)
      GCAGCCGCAGCGCGGAACTGGTGACAGAACCGTTAACCGA (P2r) TPP-RE_R:
                                     (SEQ ID. No.: 10)
      CCGGAATTCCGGTACGTACTTAGATACTACGACTAAACG
```

An entire gene fragment mixture of the polymerase chain reaction product obtained from the previous step was used as a template, and the following pair of DNA sequence segments was designed and used as a pair of primers. A polymerase chain reaction of the polymerase chain reaction product was conducted by using the pair of primers to obtain a TPSP fusion gene DNA fragment containing a trehalose-6-phosphate synthase gene (SEQ ID. No.: 3) and a trehalose-6-phosphate phosphatase gene (SEQ ID. No.: 4).

```
                                     (SEQ ID. No.: 11)
(P3f) TPSP-RE_F:     GGACTAGTCCCCCCCGGGGG (SEQ ID. No.: 12)
(P3r) TPSP-RE_R:     CCGGAATTCCGGTACGTAC
```

Then, a pJET 1.2 (Fermentas, USA) was used as a cloning vector and the "TPSP fusion gene DNA fragment" was constructed into the cloning vector by a cutting and ligating manner by using restriction enzymes and a ligase to complete pJET-TPSP.

Similarly, an *Escherichia coli* genomic DNA was used as a template, and the following pair of DNA sequence segments were designed and used as a pair of primers. A polymerase chain reaction of the *Escherichia coli* genomic DNA was conducted by using the pair of primers to obtain a DNA fragment containing an EPGI promoter.

```
                                     (SEQ ID. No.: 13)
(P4f) EPGI-P_F:     CACGGATAACGTTCGGGTAAC (SEQ ID. No.: 14)
(P4r) EPGI-P_R:     TAGCAATACTCTTCTGATTTTG
```

Next, the pJET-TPSP was used as a cloning vector and the "a DNA fragment containing an EPGI promoter" was constructed into the cloning vector by a cutting and ligating manner to complete pJET-EPGI::TPSP.

Similarly, an *Escherichia coli* genomic DNA was used as a template, and the following two pairs of DNA sequence segments were designed and used as two pairs of primers. A polymerase chain reaction of the *Escherichia coli* genomic DNA was conducted by using the pair of primers to obtain two DNA fragments, treF500L and treF500R, wherein treF500L and treF500R contain 1-500 bp and 1151-1650 bp of the cytoplasmic trehalase gene (treF gene), respectively.

| (P5f) treF-L_F: | CACGGATAACGTTCGGGTAAC | (SEQ ID. No.: 15) |
|---|---|---|
| (P5r) treF-L_R: | TAGCAATACTCTTCTGATTTTG | (SEQ ID. No.: 16) |
| (P6f) treF-R_F: | CACGGATAACGTTCGGGTAAC | (SEQ ID. No.: 17) |
| (P6r) treF-R_R: | TAGCAATACTCTTCTGATTTTG | (SEQ ID. No.: 18) |

After that, the pJET-EPGI::TPSP was used as a cloning vector and the "treF500L" and "treF500R" were constructed at the upstream end and the downstream end of the DNA fragment of EPGI::TPSP in the cloning vector, respectively by a cutting and ligating manner to complete pJET-treF500L:: EPGI::TPSP:: treF500R.

Afterward, a DNA fragment of the "treF500L::EPGI:: TPSP:: treF500R" in the pJET-treF500L::EPGI::TPSP:: treF500R circular plasmid was cut from the pJET-treF500L:: EPGI::TPSP:: treF500R circular plasmid to form a linear DNA. Then, the linear DNA was introduced into the *Escherichia coli* DH5α cells by performing an electroporation process. After that, the linear DNA was subjected to a homologous recombination mechanism in the *Escherichia coli* DH5α cells, the *Escherichia coli* DH5α cells were selected by performing colony polymerase chain reaction and immunoblot blot analysis, and a positive transformant therefrom was a bacterial strain of *Escherichia coli* capable of spontaneously accumulating self-producing trehalose therein of the invention.

The obtained bacterial strain of *Escherichia coli* was named *Escherichia coli EcDTre001* (TG), and was deposited on Nov. 11, 2010, in the German Collection of Microorganisms and Cell Cultures (Deutsche Sammlung von Mikroorganismen and Zellkulturen GmbH, DSMZ) under Accession number DSM 24175.

2. Process for Preparing Competent Cells

The obtained EcDTre001 (TG) bacterial strain of *Escherichia coli* capable of spontaneously accumulating self-producing trehalose therein of the invention was used as a source for forming competent cells. A single colony of the EcDTre001 (TG) bacterial strain was inoculated into a 5 ml LB medium to form a bacteria suspension. After being cultured under a temperature of 37° C. for 16 hours, the bacteria suspension was inoculated into a 50 ml LB medium by a ratio of 1:100 (the bacteria suspension to the LB medium) and was cultured until an absorbance of $OD_{600}$ of the bacteria suspension came close to 0.3-0.6. Then the bacteria suspension was placed into an ice bath at 0-4° C. After that, the bacteria suspension was centrifuged at 3000 rpm for several minutes, and then a supernatant of the bacteria suspension was removed to obtain a cell precipitate. A transformation agent (which was prepared according to the content described in the literature (a) Mandel, M. and Higa A. (J. Mol. Biol. 53:159)(1970), or (b) Inoue, H. (Gene 96:23)(1990)) was well mixed with the cell precipitate to form competent cells suspension. The competent cell suspension was packed into a plurality 1.5 ml centrifugetubes.

3. Transformation Process

100 µl of the competent cell suspension was thawed out and 0.1 ng of pUC19 plasmid was added to and mixed with the competent cell suspension. After addition of the pUC19 plasmid, the competent cell suspension was placed into an ice bath for 30 minutes. Then, the competent cell suspension was placed under a temperature of 42° C. for heat shock for 1.5 minutes. After heat shock, the competent cell suspension was placed into an ice bath for two minutes, poured into 900 µl of a SOC medium, and shaking cultured under a temperature of 37° C. for 45 minutes to form a cultured competent cell suspension. Afterward, the cultured competent cell suspension was spread on an LB agar plate containing a specific antibiotic.

EXAMPLES

Example 1

Example 1 is an example showing the transformation efficiency differences between the competent cells prepared by conventional DH5α cells (WT) and EcDTre001 cells (TG) of the invention after being stored at a relatively higher temperature (−20° C.).

Commercially available conventional DH5α cells (WT) and EcDTre001 cells (TG) of the invention were selected as host cells for preparing the competent cells. The DH5α cells (WT) and the EcDTre001 cells (TG) were used to prepare the competent cells according to the process for preparing competent cells with a transformation agent prepared according to the content described in the literature (a) Mandel, M. and Higa A. (J. Mol. Biol. 53:159)(1970) (hereafter referred to as process (a)), respectively. After that, two groups of competent cell suspensions, the WT competent cell suspension and the TG competent cell suspension were obtained, respectively.

The two groups of competent cell suspensions were placed under a temperature of −20° C. to be stored at a period of 6 months. All competent cell suspensions were taken out from the refrigerator, and were transformed according to the transformation process by using pUC 19 as plasmids at month 0 to month 6. The results of the transformation efficiency for the two groups of competent cell are shown in FIG. 1.

FIG. 1 shows that the competent cells prepared from the EcDTre001 cells (TG) of the invention maintained an original transformation efficiency thereof during a 6 month storage period under a temperature of −20° C. It was confirmed that the competent cells prepared from the EcDTre001 cells (TG) were not limited to being stored at temperatures of −70° C. to −80° C. for storing competent cells.

Example 2

Example 2 is an example showing competent cells prepared from the genetic modified EcDTre001 cells (TG) of the invention by different preparation processes and the transformation efficiency difference therebetween.

Commercially available conventional DH5α cells (WT) and EcDTre001 cells (TG) of the invention were selected as host cells for preparing competent cells. The DH5α cells (WT) and the EcDTre001 cells (TG) were used to prepare the competent cells according to the process for preparing competent cells with a transformation agent prepared according to the content described in the literature (a) Mandel, M. and Higa A. (J. Mol. Biol. 53:159)(1970) (hereafter referred to as process (a)), respectively, and the DH5α cells (WT) and the EcDTre001 cells (TG) were used to prepare the competent cells according to the process for preparing competent cells with a transformation agent prepared according to the content described in the literature (b) Inoue, H. (Gene 96:23)(1990) (hereafter referred to as process (b)), respectively. After that, the four competent cell suspension groups, (a) WT, (a) TG, (b) WT and (b) TG were obtained, respectively.

Each of the four competent cell suspension groups, (a) WT, (a) TG, (b) WT and (b) TG was placed under a temperature of −80° C. and a temperature of −20° C. to be stored, respectively for a period of 6 months. All competent cell suspensions were taken out from the refrigerators, and were transformed according to the transformation process by using pUC 19 as plasmids at month 0 to month 6. The results of the transformation efficiency for each of the four competent cell groups are shown in FIG. 2.

Figure 2:
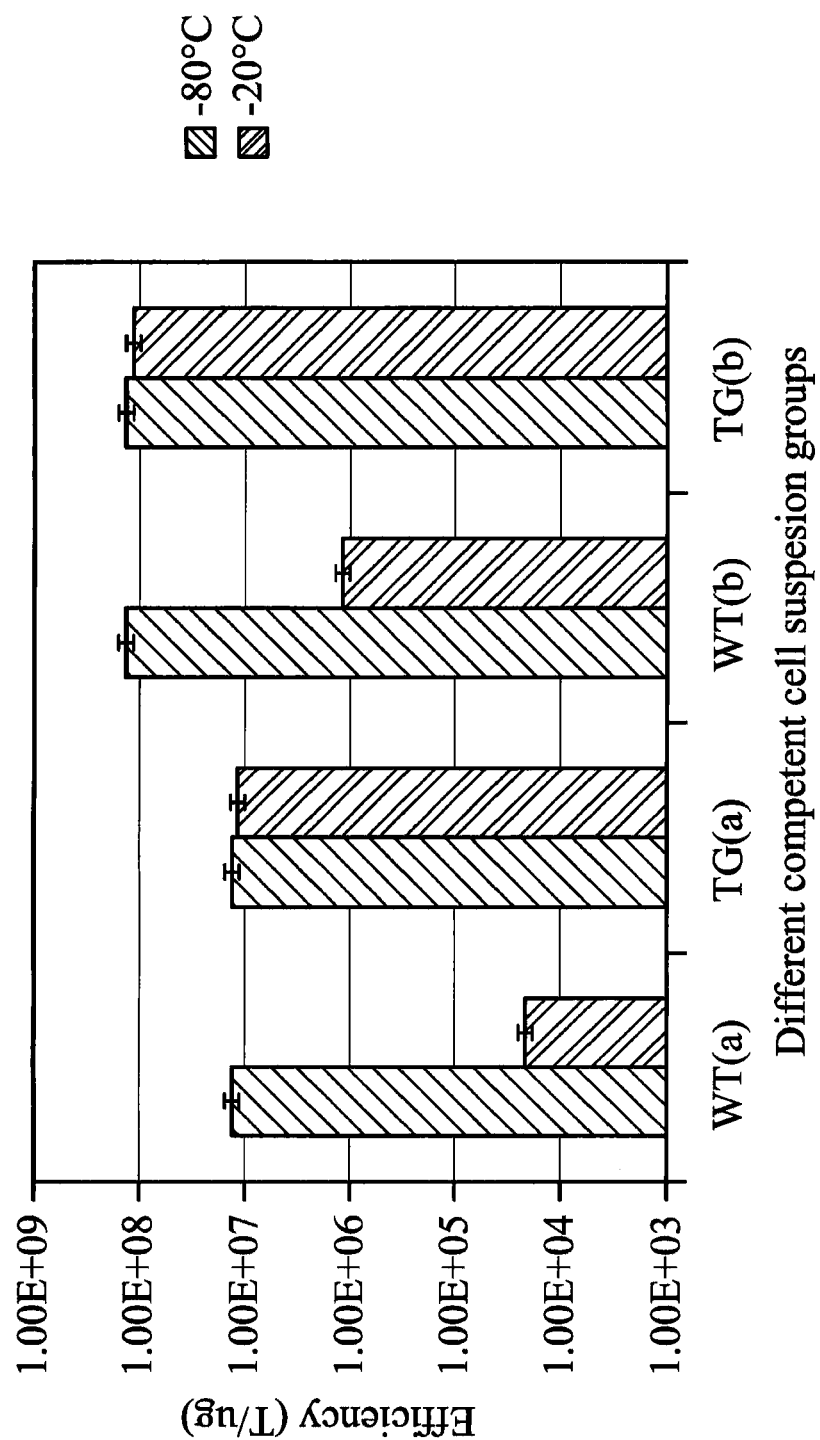
FIG. 2 is a bar chart showing stability differences between the transformation efficiency of the four competent cell suspension groups, (a) WT, (a) TG, (b) WT and (b) TG during a 6 month storing period under a temperature of −80° C. and −20° C.

FIG. 2 shows that competent cells prepared from the EcDTre001 cells (TG) of the invention by using the process (a) and competent cells prepared from the EcDTre001 cells (TG) of the invention by using the process (b) all maintained original transformation efficiencies thereof during a 6 month storage period under a temperature of −80° C. or −20° C. It was confirmed that the competent cells prepared from the EcDTre001 cells (TG) had stable transformation efficiency.

Example 3

Effect on the Transformation Efficiency of Prepared Competent Cells by Adding a Solid Sphere into Competent Cells Suspension Containing a Transformation Agent Commercially available conventional DH5α cells (WT) and EcDTre001 cells (TG) of the invention were selected as host cells for preparing the competent cells. The DH5α cells (WT) and the EcDTre001 cells (TG) were used to prepare the competent cells according to the process for preparing competent cells with a transformation agent prepared according to the content described in the literature (b) Inoue, H. (Gene 96:23)(1990) (hereafter referred to as process (b)), respectively. After that, two groups of competent cell suspensions, the WT competent cell suspension and the TG competent cell suspension were obtained, respectively. Next the WT competent cell suspension was separated into two groups, wherein 3 aluminum beads with a particle diameter of 5 mm pre-refrigerated at 4° C., were added into one of the two groups to form a group of the competent cell suspension, WT-B, and the TG competent cell suspension was separated into two groups, wherein 3 aluminum beads with a particle diameter of 5 mm, pre-refrigerated at 4° C., were added to one of the two group to form a group of competent cell suspensions, TG-B. After that, the four competent cell suspension groups, WT, WT-B, TG and the TG-B were obtained, respectively.

Figure 3A:
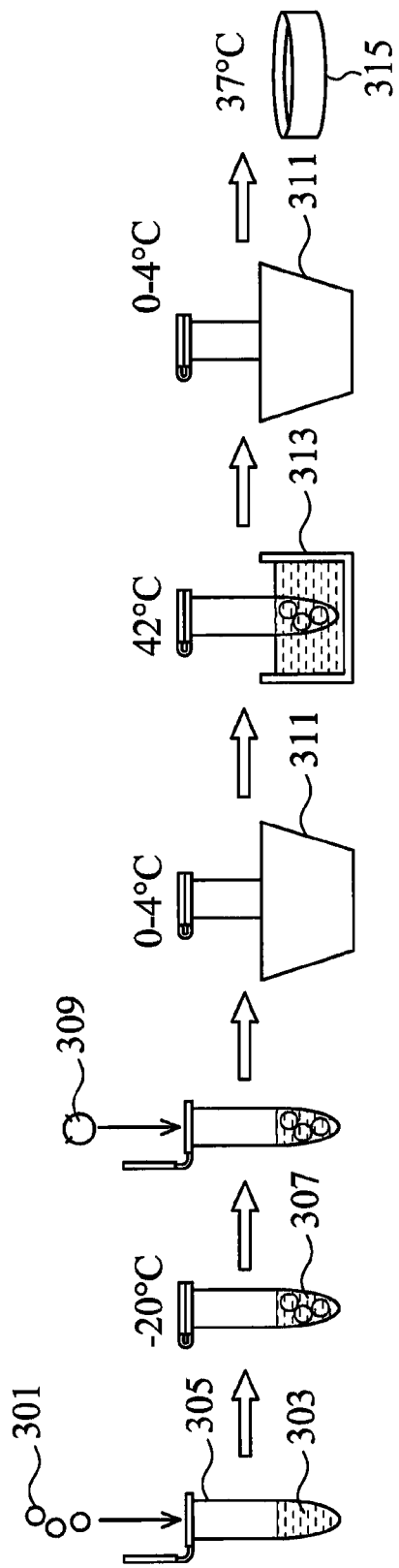
FIG. 3A shows the transformation process for competent cells of the WT-B group and competent cells of the TG-B group in Example 3.
Figure 3B:
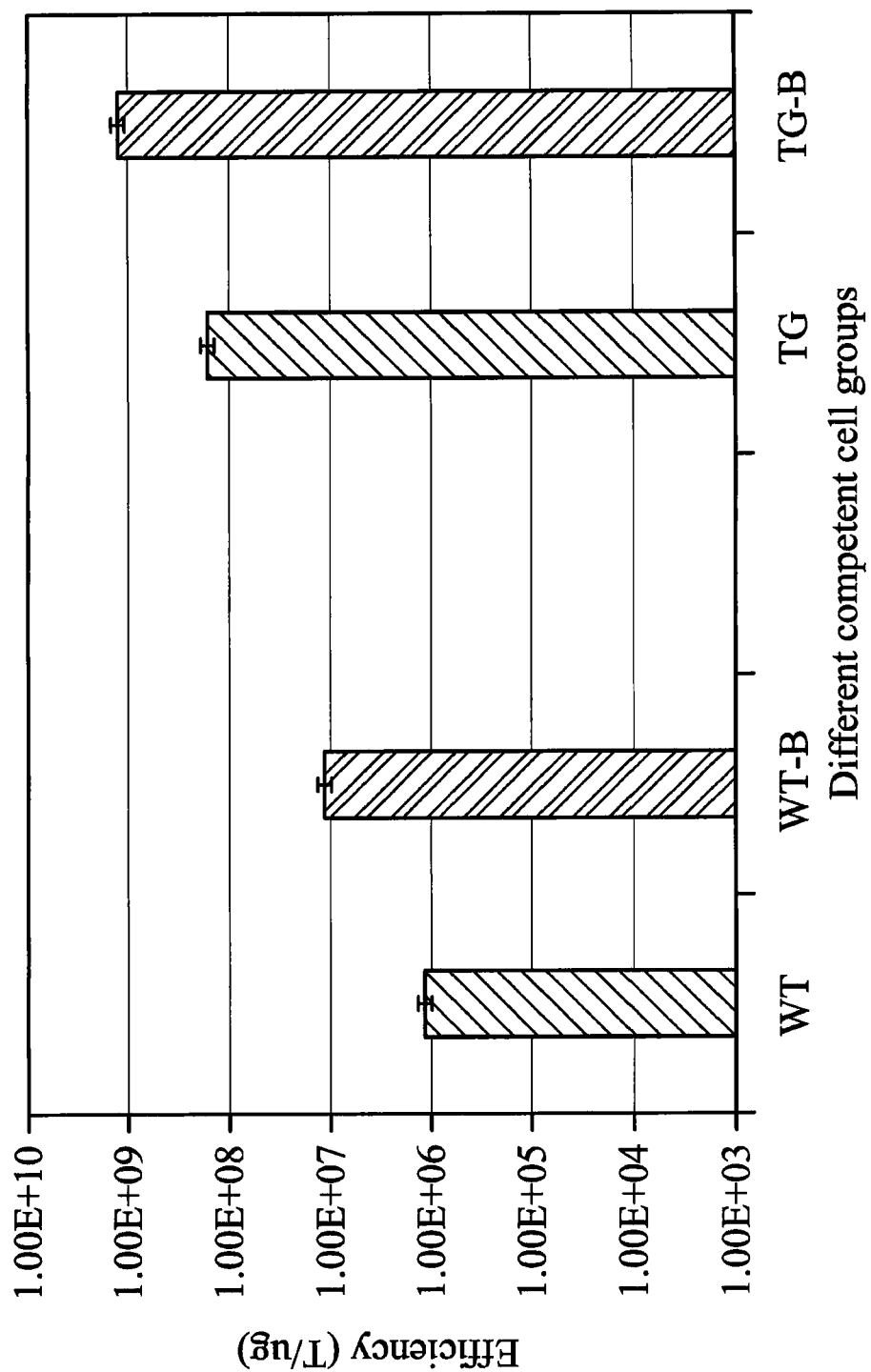
FIG. 3B is a bar chart showing the difference between transformation efficiency of the four competent cell suspension groups, WT, WT-B, TG and TG-B after being stored for 6 months under a temperature of −20° C.

The four competent cell suspension groups were placed under a temperature of −20° C. to be stored. After 6 months, all competent cell suspensions were taken out from the refrigerators, and were transformed according to the transformation process by using pUC 19 as plasmids, wherein the time for performing the heat shock process of the transformation process was reduced to be 20 seconds and aluminum beads in the WT-B competent cell suspension and the TG-B competent cell suspension were directly used as spreaders for spreading the WT-B competent cell suspension and the TG-B competent cell suspension on the LB agar plate, respectively. The transformation process for competent cells of the WT-B group and competent cells of the TG-B group is shown in FIG. 3A. The results of the transformation efficiency for the four competent cell groups are shown in FIG. 3B. FIG. 3A shows that there aluminum beads 301 were added into a tube 305 containing competent cells suspension 303. Next, the tube 301, containing a mixture 307 of the competent cell suspension and aluminum beads, was stored under a temperature of −20° C. for 6 months. Then, the competent cells were transformed by using pUC 19 as plasmids. First, the mixture 307 of the competent cell suspension and aluminum beads was thawed out and the plasmids 309 were added therein. After that, the mixture 307 of the competent cell suspension and aluminum beads was placed into an ice bath 311 for 30 minutes. Then, the mixture 307 of the competent cell suspension and aluminum beads was placed under a temperate of 42° C. for 20 seconds to perform heat shock 313. After heat shock 313 was performed, the mixture 307 of the competent cell suspension and aluminum beads was placed into an ice bath 311 for 2 minutes, poured into 900 μl of a SOC medium, and shaking cultured under a temperature of 37° C. for 45 minutes. After being cultured, the mixture 307 of the competent cell suspension and aluminum beads was spread on an LB agar plate 315 containing a specific antibiotic.

FIG. 3B shows that after being stored at a relatively higher temperature of −20° C. for 6 months, competent cells of the TG group and competent cells of the TG-B group of the were not limited to being stored at temperatures of −70° C. to −80° C. for storing competent cells. Moreover, transformation efficiency of the competent cell suspensions of the WT-B group and the TG-B group (containing aluminum beads) was raised 3-10 times, respectively, as compared with that of the WT group and the TG group (not containing aluminum beads). Moreover, the transformation efficiency of the competent cell suspensions of the TG-B group reached $1.5 \times 10^9$ transformants/m plasmid DNA.

Example 4

Effect of Using Different Material for a Solid Sphere on the Transformation Efficiency of the Competent Cells EcDTre001 cells (TG) of the invention were selected as host cells for preparing competent cells. The EcDTre001 cells (TG) was used to prepare the competent cells according to the process for preparing competent cells with a transformation agent prepared according to the content described in the literature (b) Inoue, H. (Gene 96:23)(1990) (hereafter referred to as process (b)), wherein 3 solid spheres with a particle diameter of 5 mm and good thermal conductivity, pre-refrigerated at 4° C., were added into the competent cell suspension. The four competent cell suspension groups prepared in the example were competent cell suspensions containing "glass beads", "stainless steel beads", "aluminum beads" and "no bead", respectively.

The four competent cell suspension groups were placed under a temperature of −20° C. to be stored. After 6 months, all competent cell suspensions were taken out from the refrigerator, and were transformed according to the transformation process by using pUC 19 as plasmids. The results of the transformation efficiency for the four competent cell groups are shown in Table 2.

TABLE 2

Effect of using different exemplificative material for a solid sphere on the transformation efficiency of the competent cells

| Material of solid spheres | Thermal conductivity | Transformation efficiency (transformants/ μg plasmid DNA) |
| --- | --- | --- |
| No bead | Poor | $1.20 \times 10^8$ |
| Glass beads | Not bad | $1.86 \times 10^8$ |
| Stainless steel beads | Good | $4.68 \times 10^8$ |
| Aluminum beads | Best | $1.27 \times 10^9$ |

Table 2 shows that all of the examples of the solid sphere additions with different materials into the competent cell suspension increased the transformation efficiency of the competent cells.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A bacterial strain of *Escherichia coli* deposited in the German Collection of Microorganisms and Cell Cultures (DSMZ) under Accession number DSM 24175, wherein the bacterial strain of *Escherichia coli* is capable of accumulating self-producing trehalose therein.

2. A method for preparing competent cells, comprising:
culturing the cell for preparing competent cells as claimed in claim 1 to obtain a cell suspension;
placing the cell suspension into an ice bath;
centrifuging the cell suspension to obtain a cell precipitate;
mixing a pre-treating agent with the cell precipitate; and
obtaining competent cells suspension.

3. The method for preparing competent cells as claimed in claim 2, wherein the competent cell suspension is capable of being stored at a temperature of lower than −10° C.

4. The method for preparing competent cells as claimed in claim 2, wherein the competent cell suspension is capable of being stored under a temperature of −20° C.

5. The method for preparing competent cells as claimed in claim 2, further comprising adding at least one solid sphere into the competent cell suspension.

6. The method for preparing competent cells as claimed in claim 5, wherein the solid sphere is composed of materials comprising glass, ceramics, stainless steel, iron or aluminum.

7. The method for preparing competent cells as claimed in claim 5, wherein a particle diameter of the solid sphere is about 2-6 mm.

* * * * *

SEQUENCE LISTING

<160> NUMBER OF SEQ ID NOS: 18

<210> SEQ ID NO 1
<211> LENGTH: 474
<212> TYPE: PRT
<213> ORGANISM: Escherichia coli

<400> SEQUENCE: 1

```
Met Ser Arg Leu Val Val Ser Asn Arg Ile Ala Pro Pro Asp Glu
1               5                   10                  15

His Ala Ala Ser Ala Gly Gly Leu Ala Val Gly Ile Leu Gly Ala Leu
                20                  25                  30

Lys Ala Ala Gly Gly Leu Trp Phe Gly Trp Ser Gly Glu Thr Gly Asn
            35                  40                  45

Glu Asp Gln Pro Leu Lys Val Lys Lys Gly Asn Ile Thr Trp Ala
        50                  55                  60

Ser Phe Asn Leu Ser Glu Gln Asp Leu Asp Glu Tyr Tyr Asn Gln Phe
65                  70                  75                  80

Ser Asn Ala Val Leu Trp Pro Ala Phe His Tyr Arg Leu Asp Leu Val
                85                  90                  95

Gln Phe Gln Arg Pro Ala Trp Asp Gly Tyr Leu Arg Val Asn Ala Leu
            100                 105                 110

Leu Ala Asp Lys Leu Leu Pro Leu Leu Gln Asp Asp Ile Ile Trp
        115                 120                 125

Ile His Asp Tyr His Leu Leu Pro Phe Ala His Glu Leu Arg Lys Arg
        130                 135                 140

Gly Val Asn Asn Arg Ile Gly Phe Phe Leu His Ile Pro Phe Pro Thr
145                 150                 155                 160

Pro Glu Ile Phe Asn Ala Leu Pro Thr Tyr Asp Thr Leu Leu Glu Gln
                165                 170                 175

Leu Cys Asp Tyr Asp Leu Leu Gly Phe Gln Thr Glu Asn Asp Arg Leu
            180                 185                 190

Ala Phe Leu Asp Cys Leu Ser Asn Leu Thr Arg Val Thr Thr Arg Ser
        195                 200                 205

Ala Lys Ser His Thr Ala Trp Gly Lys Ala Phe Arg Thr Glu Val Tyr
    210                 215                 220

Pro Ile Gly Ile Glu Pro Lys Glu Ile Ala Lys Gln Ala Ala Gly Pro
225                 230                 235                 240

Leu Pro Pro Lys Leu Ala Gln Leu Lys Ala Glu Leu Lys Asn Val Gln
                245                 250                 255

Asn Ile Phe Ser Val Glu Arg Leu Asp Tyr Ser Lys Gly Leu Pro Glu
            260                 265                 270

Arg Phe Leu Ala Tyr Glu Ala Leu Leu Glu Lys Tyr Pro Gln His His
        275                 280                 285

Gly Lys Ile Arg Tyr Thr Gln Ile Ala Pro Thr Ser Arg Gly Asp Val
    290                 295                 300

Gln Ala Tyr Gln Asp Ile Arg His Gln Leu Asn Glu Ala Gly Arg
305                 310                 315                 320

Ile Asn Gly Lys Tyr Gly Gln Leu Gly Trp Thr Pro Leu Tyr Tyr Leu
                325                 330                 335

Asn Gln His Phe Asp Arg Lys Leu Leu Met Lys Ile Phe Arg Tyr Ser
            340                 345                 350

Asp Val Gly Leu Val Thr Pro Leu Arg Asp Gly Met Asn Leu Val Ala
        355                 360                 365
```

```
Lys Glu Tyr Val Ala Ala Gln Asp Pro Ala Asn Pro Gly Val Leu Val
        370                 375                 380

Leu Ser Gln Phe Ala Gly Ala Ala Asn Glu Leu Thr Ser Ala Leu Ile
385                 390                 395                 400

Val Asn Pro Tyr Asp Arg Asp Glu Val Ala Ala Leu Asp Arg Ala
                405                 410                 415

Leu Thr Met Ser Leu Ala Glu Arg Ile Ser Arg His Ala Glu Met Leu
                420                 425                 430

Asp Val Ile Val Lys Asn Asp Ile Asn His Trp Gln Glu Cys Phe Ile
            435                 440                 445

Ser Asp Leu Lys Gln Ile Val Pro Arg Ser Ala Glu Ser Gln Gln Arg
    450                 455                 460

Asp Lys Val Ala Thr Phe Pro Lys Leu Ala
465                 470
```

<210> SEQ ID NO 2
<211> LENGTH: 266
<212> TYPE: PRT
<213> ORGANISM: Escherichia coli

<400> SEQUENCE: 2

```
Met Thr Glu Pro Leu Thr Glu Thr Pro Glu Leu Ser Ala Lys Tyr Ala
1               5                   10                  15

Trp Phe Phe Asp Leu Asp Gly Thr Leu Ala Glu Ile Lys Pro His Pro
            20                  25                  30

Asp Gln Val Val Pro Asp Asn Ile Leu Gln Gly Leu Gln Leu Leu
        35                  40                  45

Ala Thr Ala Ser Asp Gly Ala Leu Ala Leu Ile Ser Gly Arg Ser Met
    50                  55                  60

Val Glu Leu Asp Ala Leu Ala Lys Pro Tyr Arg Phe Pro Leu Ala Gly
65                  70                  75                  80

Val His Gly Ala Glu Arg Arg Asp Ile Asn Gly Lys Thr His Ile Val
                85                  90                  95

His Leu Pro Asp Ala Ile Ala Arg Asp Ile Ser Val Gln Leu His Thr
                100                 105                 110

Val Ile Ala Gln Tyr Pro Gly Ala Glu Leu Glu Ala Lys Gly Met Ala
            115                 120                 125

Phe Ala Leu His Tyr Arg Gln Ala Pro Gln His Glu Asp Ala Leu Met
130                 135                 140

Thr Leu Ala Gln Arg Ile Thr Gln Ile Trp Pro Gln Met Ala Leu Gln
145                 150                 155                 160

Gln Gly Lys Cys Val Val Glu Ile Lys Pro Arg Gly Thr Ser Lys Gly
                165                 170                 175

Glu Ala Ile Ala Ala Phe Met Gln Glu Ala Pro Phe Ile Gly Arg Thr
            180                 185                 190

Pro Val Phe Leu Gly Asp Asp Leu Thr Asp Glu Ser Gly Phe Ala Val
        195                 200                 205

Val Asn Arg Leu Gly Gly Met Ser Val Lys Ile Gly Thr Gly Ala Thr
    210                 215                 220

Gln Ala Ser Trp Arg Leu Ala Gly Val Pro Asp Val Trp Ser Trp Leu
225                 230                 235                 240

Glu Met Ile Thr Thr Ala Leu Gln Gln Lys Arg Glu Asn Asn Arg Ser
                245                 250                 255

Asp Asp Tyr Glu Ser Phe Ser Arg Ser Ile
            260                 265
```

```
<210> SEQ ID NO 3
<211> LENGTH: 1424
<212> TYPE: DNA
<213> ORGANISM: Escherichia coli

<400> SEQUENCE: 3
tgagtcgttt agtcgtagta tctaaccgga ttgcaccacc agacgagcac gccgccagtg      60
ccggtggcct tgccgttggc atactggggg cactgaaagc cgcaggcgga ctgtggtttg     120
gctggagtgg tgaaacaggg aatgaggatc agccgctaaa aaaggtgaaa aaggtaaca     180 ttacgtgggc ctcttttaac ctcagcgaac aggaccttga cgaatactac aaccaattct     240
ccaatgccgt tctctggccc gcttttcatt atcggctcga tctggtgcaa tttcagcgtc     300
ctgcctggga cggctatcta cgcgtaaatg cgttgctggc agataaatta ctgccgctgt     360
tgcaagacga tgacattatc tggatccacg attatcacct gttgccattt gcgcatgaat     420
tacgcaaacg gggagtgaat aatcgcattg gtttctttct gcatattcct ttcccgacac     480
cggaaatctt caacgcgctg ccgacatatg acaccttgct tgaacagctt tgtgattatg     540
atttgctggg tttccagaca gaaaacgatc gtctggcgtt cctggattgt ctttctaacc     600
tgaccccgcg tcacgacacgt agcgcaaaaa gccatacagc ctggggcaaa gcatttcgaa     660
cagaagtcta cccgatcggc attgaaccga agaaatagc caaacaggct gccgggccac     720
tgccgccaaa actggcgcaa cttaaagcgg aactgaaaaa cgtacaaaat atcttttctg     780
tcgaacggct ggattattcc aaaggtttgc cagagcgttt tctcgcctat gaagcgttgc     840
tggaaaaata tccgcagcat catggtaaaa ttcgttatac ccagattgca ccaacgtcgc     900
gtggtgatgt gcaagcctat caggatattc gtcatcagct cgaaaatgaa gctggacgaa     960
ttaatggtaa atacgggcaa ttaggctgga cgccgcttta ttatttgaat cagcattttg    1020
accgtaaatt actgatgaaa atattccgct actctgacgt gggcttagtg acgccactgc    1080
gtgacgggat gaacctggta gcaaaagagt atgttgctgc tcaggaccca gccaatccgg    1140
gcgttcttgt tctttcgcaa tttgcgggag cggcaaacga gttaacgtcg cgttaattg    1200 ttaaccccta cgatcgtgac gaagttgcag ctgcgctgga tcgtgcattg actatgtcgc    1260
tggcggaacg tatttcccgt catgcagaaa tgctggacgt tatcgtgaaa aacgatatta    1320
accactggca ggagtgcttc attagcgacc taaagcagat agttccgcga agcgcggaaa    1380
gccagcagcg cgataaagtt gctacctttc caaagcttgc gtag                     1424

<210> SEQ ID NO 4
<211> LENGTH: 801
<212> TYPE: DNA
<213> ORGANISM: Escherichia coli

<400> SEQUENCE: 4
atgacagaac cgttaaccga aacccctgaa ctatccgcga aatatgcctg gttttttgat      60
cttgatggaa cgctggcgga aatcaaaccg catcccgatc aggtcgtcgt gcctgacaat     120
attctgcaag gactacagct actggcaacc gcaagtgatg gtgcattggc attgatatca     180
gggcgctcaa tggtggagct tgacgcactg gcaaaacctt atcgcttccc gttagcgggc     240
gtgcatgggg cggagcgccg tgacatcaat ggtaaaacac atatcgttca tctgccggat     300
gcgattgcgc gtgatattag cgtgcaactg catacagtca tcgctcagta tcccggcgcg     360
gagctggagg cgaaagggat ggcttttgcg ctgcattatc gtcaggctcc gcagcatgaa     420
gacgcattaa tgcacattag caacgtatt actcagatct ggccacaaat ggcgttacag     480
cagggaaagt gtgttgtcga gatcaaaccg agaggtacca gtaaaggtga ggcaattgca     540
```

| | |
|---|---|
| gcttttatgc aggaagctcc ctttatcggg cgaacgcccg tatttctggg cgatgattta | 600 |
| accgatgaat ctggcttcgc agtcgttaac cgactgggcg aatgtcagt aaaaattggc | 660 |
| acaggtgcaa ctcaggcatc atggcgactg gcgggtgtgc cggatgtctg gagctggctt | 720 |
| gaaatgataa ccaccgcatt acaacaaaaa agagaaaata acaggagtga tgactatgag | 780 |
| tcgtttagtc gtagtatcta a | 801 |

<210> SEQ ID NO 5
<211> LENGTH: 1650
<212> TYPE: DNA
<213> ORGANISM: Escherichia coli

<400> SEQUENCE: 5

| | |
|---|---|
| atgctcaatc agaaaattca aaaccctaat ccagacgaac tgatgatcga agtcgatctc | 60 |
| tgctatgagc tggacccgta tgaattaaaa ctggatgaga tgatcgaggc agaaccggaa | 120 |
| cccgagatga ttgaagggct gcctgcctct gatgcgctga cgcctgccga tcgctatctc | 180 |
| gaactgttcg agcatgttca gtcggcgaaa attttccccg acagtaaaac ctttcccgac | 240 |
| tgcgcaccta aaatggaccc gctggatatc ttaatccgct accgtaaagt gcgccgtcat | 300 |
| cgtgattttg acttgcgcaa gtttgttgaa aaccacttct ggctgccgga ggtctactcc | 360 |
| agcgagtatg tatcggaccc gcaaaattcc ctgaaagagc atatcgacca gctgtggccg | 420 |
| gtgctaaccc gcgaaccaca ggatcacatt ccgtggtctt ctctgctggc gctgccgcag | 480 |
| tcatatattg tcccgggcgg ccgttttagc gaaacctact attgggattc ctatttcacc | 540 |
| atgctggggc tggcggaaag tggtcgggaa gatttgctga aatgcatggc cgataacttc | 600 |
| gcctggatga tcgaaaacta cggtcacatc cccaacggca accgcaccta ttatttgagc | 660 |
| cgctcgcaac caccggtttt tgcgctgatg gtggagttgt ttgaagaaga tggtgtacgc | 720 |
| ggtgcgcgcc gctatctcga ccaccttaaa atggaatatg ccttctggat ggacggtgca | 780 |
| gaatcgttaa tccctaatca ggcctatcgc catgttgtgc ggatgccgga cggatcgctg | 840 |
| ctcaaccgtt actgggacga tcgcgacacg ccgcgtgacg aatcctggct tgaggacgtt | 900 |
| gaaaccgcga acattctggt cgcccgcccc aacgaggtga ccgcgatttt acgcgcgggg | 960 |
| gcggcctccg gttgggatta ctcttcccgt tggctgcgtg atactggtcg tctggcgagc | 1020 |
| attcgtacca cccagttcat ccccatcgat ctgaatgcct tcctgtttaa actggagagc | 1080 |
| gccatcgcca acatctcggc gctgaaaggc gagaaagaga cagaagcact gttccgccag | 1140 |
| aaaagccagtg cccgtcgcga tgcggtaaac cgttacctct gggatgatga aaacggcatc | 1200 |
| taccgcgatt acgactggcg acgcgaacaa ctggcgctgt tttccgctgc cgccattgtg | 1260 |
| ccactctatg tcggtatggc gaaccatgaa caggccgatc gtctggcaaa cgccgtgcgc | 1320 |
| agtcggttac tgacacctgg cgggattctg gcaagcgagt acgaaaccgg tgaacagtgg | 1380 |
| gataaaccca acggctgggc accgttacaa tggatggcga ttcagggatt taaaatgtac | 1440 |
| ggcgatgacc ttctgggtga tgaaatcgcg cgaagctggc tgaagacggt gaatcagttc | 1500 |
| tatctggaac agcacaaaact gatcgaaaaa taccatattg ccgatggtgt tccccgcgaa | 1560 |
| ggcggcggtg gcgagtatcc gttgcaggat gggtttggct ggactaacgg tgtggtacgc | 1620 |
| cgtttaattg gtttgtacgg cgaaccataa | 1650 |

<210> SEQ ID NO 6
<211> LENGTH: 1698
<212> TYPE: DNA
<213> ORGANISM: Escherichia coli

<400> SEQUENCE: 6

```
ttaaggtgtg ggttgtgcct ctttggttga gggttgcgtc gttgctgact taacggtcgg    60
acgcgtcgcc ggaacattgt cacacggttg ctctttcggg cagatcaaat ccagcatttt   120
cagcgtcacg ccattggtcc agccaaagcc atcctgtaat ggatattcgc caccgccgcc   180
ccccgttccg gtggtgctga catcatattt ttccaccagc ttttctccc ggtcataggt    240
gtgctgaaca ttggtcagga agtgccagct aatgtccatc gccacctctt tttgcccgta   300
gttttgtaat ccttctgtcg cgacccactg taacggtgcc cagccatttg gcgcatccca   360
ttgttgccca cttttcaccg acgtggtgtt caggccgccg ggttgcagca gatgtgtttt   420
cgtcgccgtc gccattttgt tggcgcgatc tttcgctgcc gcattgacgt acagcgggaa   480
cagggcggcc gcggttaact gattgcgcac tttatgactt ttcaggtcgt aatcggcata   540
ccagccttgt tgatcgttcc acaggtattt ttcgatccct ttttgacggg catttgccag   600
cgtttcgtac tggtttgcca tcgcgttatc tccggcagct ttgctggcgc gggcgaggat   660
tttttccatt ttaaacatca ggctgttcag atcgaccggt acgatgctgg tggtgcgtaa   720
ggtatttaac tgctgcgggt tgtccatcca gcgcgagctg aaatcccagc cagacgcagc   780
ggcagagcgc aggtcgcggt aaatttcagt ggcaggtcga ttcggattgc ttttggcggt   840
ggcaatatct tccacccatg actctggtcg tggcgtatcg cgatcgtccc agtagcggtt   900
gagaagggta ccatcctgaa gtttgacaac gcgttttttcc tgttgtccgg cttgcaggtt   960
ttcaacaccg tccatccagt aagcatattc ttttttgcatt tgcggcaggt attgcttcaa  1020
cgcggcatcg ccttcatgct gcgccagtaa ctctaccatc agggcaaaga agggcggttg  1080
cgagcggctt aaatagtaac tgcggttgcc gttgggaata tgaccgtaag tgtctatttc  1140
atgagcaaaa ttggccacca tatccgcgac tttatcccag tgaccgcttt cggcaagtcc  1200
taacatggtg aagtaactgt cccagtaata tacctcgcga aagcgtccgc ccggcacgac  1260
ataaggttcc ggcagcggta acagagaatc ccattttttcg gtgttttcgg tagaacgcgt  1320
taataccggc caaagtccgt caatatgttc gcgcagtgac tgcccctctg gcggaacata  1380
tttctcgcct tctttcggca gggtgaaatt gacgttaacg aaatggcgca gatcaaatcc  1440
gctctggttt tgctgcatcc gataatcagc aaggatcatc agcggatcgc tgttcggcac  1500
ggcatcggca aaggttttt ggtccggaaa agtttggcg ttttgcacat cattaaacag   1560
cggccctaat aaaatatcag gcggctgtgg tgttaccggt gtttcttctg cctgcaccga  1620
tagcgcagcg aaacacaaaa agatacaggc tggaattaac gccattttt gcgggcgaga  1680
aggtgcgggg gatttcat                                                1698
```

<210> SEQ ID NO 7
<211> LENGTH: 40
<212> TYPE: DNA
<213> ORGANISM: Artificial
<220> FEATURE:
<223> OTHER INFORMATION: Artificial primer

<400> SEQUENCE: 7

```
ggactagtcc cccccggggg atgagtcgtt tagtcgtagt                           40
```

<210> SEQ ID NO 8
<211> LENGTH: 40
<212> TYPE: DNA
<213> ORGANISM: Artificial
<220> FEATURE:
<223> OTHER INFORMATION: Artificial primer

<400> SEQUENCE: 8
tccgcgctgc ggctgcccag cgcaagcttt ggaaaggtag          40

<210> SEQ ID NO 9
<211> LENGTH: 40
<212> TYPE: DNA
<213> ORGANISM: Artificial
<220> FEATURE:
<223> OTHER INFORMATION: Artificial primer

<400> SEQUENCE: 9
gcagccgcag cgcggaactg gtgacagaac cgttaaccga          40

<210> SEQ ID NO 10
<211> LENGTH: 39
<212> TYPE: DNA
<213> ORGANISM: Artificial
<220> FEATURE:
<223> OTHER INFORMATION: Artificial primer

<400> SEQUENCE: 10
ccggaattcc ggtacgtact tagatactac gactaaacg           39

<210> SEQ ID NO 11
<211> LENGTH: 20
<212> TYPE: DNA
<213> ORGANISM: Artificial
<220> FEATURE:
<223> OTHER INFORMATION: Artificial primer

<400> SEQUENCE: 11
ggactagtcc cccccggggg                                20

<210> SEQ ID NO 12
<211> LENGTH: 19
<212> TYPE: DNA
<213> ORGANISM: Artificial
<220> FEATURE:
<223> OTHER INFORMATION: Artificial primer

<400> SEQUENCE: 12
ccggaattcc ggtacgtac                                 19

<210> SEQ ID NO 13
<211> LENGTH: 21
<212> TYPE: DNA
<213> ORGANISM: Artificial
<220> FEATURE:
<223> OTHER INFORMATION: Artificial primer

<400> SEQUENCE: 13
cacggataac gttcgggtaa c                              21

<210> SEQ ID NO 14
<211> LENGTH: 22
<212> TYPE: DNA
<213> ORGANISM: Artificial
<220> FEATURE:
<223> OTHER INFORMATION: Artificial primer

<400> SEQUENCE: 14
tagcaatact cttctgattt tg                             22

-continued

```
<210> SEQ ID NO 15
<211> LENGTH: 21
<212> TYPE: DNA
<213> ORGANISM: Artificial
<220> FEATURE:
<223> OTHER INFORMATION: Artificial primer

<400> SEQUENCE: 15
cacggataac gttcgggtaa c                                              21

<210> SEQ ID NO 16
<211> LENGTH: 22
<212> TYPE: DNA
<213> ORGANISM: Artificial
<220> FEATURE:
<223> OTHER INFORMATION: Artificial primer

<400> SEQUENCE: 16
tagcaatact cttctgattt tg                                             22

<210> SEQ ID NO 17
<211> LENGTH: 21
<212> TYPE: DNA
<213> ORGANISM: Artificial
<220> FEATURE:
<223> OTHER INFORMATION: Artificial primer

<400> SEQUENCE: 17
cacggataac gttcgggtaa c                                              21

<210> SEQ ID NO 18
<211> LENGTH: 22
<212> TYPE: DNA
<213> ORGANISM: Artificial
<220> FEATURE:
<223> OTHER INFORMATION: Artificial primer

<400> SEQUENCE: 18
tagcaatact cttctgattt tg                                             22
```